United States Patent [19]

Guth

[11] Patent Number: 5,798,650

[45] Date of Patent: Aug. 25, 1998

[54] PROCESS AND DEVICE FOR DETERMINING THE MASS FRACTION OF ONE CONSTITUENT OF A LAYER, AND EFFECTING THE QUALITY CONTROL OF A COMPOSITE METAL SHEET

[75] Inventor: Jérôme Guth, Metz, France

[73] Assignee: Sollac, Puteaux, France

[21] Appl. No.: 812,697

[22] Filed: Mar. 6, 1997

[30] Foreign Application Priority Data

Mar. 8, 1996 [FR] France ................. 96 02979

[51] Int. Cl.⁶ .......................... G01R 27/02; G01N 27/02
[52] U.S. Cl. ................... 324/663; 324/677; 324/701; 324/704; 324/711
[58] Field of Search ......................... 324/663, 671, 324/675, 677, 682, 693, 699, 701, 704, 713, 716, 717, 718

[56] References Cited

U.S. PATENT DOCUMENTS

| | | | |
|---|---|---|---|
| 2,528,342 | 10/1950 | Cuckler | 324/701 |
| 3,355,664 | 11/1967 | Panke | 324/671 |
| 3,535,631 | 10/1970 | Geest et al. | 324/701 |
| 4,968,947 | 11/1990 | Thom | 324/701 |
| 5,212,982 | 5/1993 | Macchiarulo et al. | 324/701 |
| 5,508,622 | 4/1996 | Gatzlaff | 324/701 |

FOREIGN PATENT DOCUMENTS

| | | |
|---|---|---|
| 0 089 435 A3 | 9/1983 | European Pat. Off. . |
| 0 219 104 A2 | 4/1987 | European Pat. Off. . |
| 0 324 193 A1 | 7/1989 | European Pat. Off. . |
| 0 394 128 A2 | 10/1990 | European Pat. Off. . |
| 0 459 875 A1 | 12/1991 | European Pat. Off. . |
| 0 493 123 A1 | 7/1992 | European Pat. Off. . |
| 0 559 527 A1 | 9/1993 | European Pat. Off. . |
| 2 158 255 | 11/1985 | United Kingdom . |

*Primary Examiner*—Diep N. Do
*Attorney, Agent, or Firm*—Oblon, Spivak, McClelland, Maier & Neustadt, P.C.

[57] ABSTRACT

A process for controlling the weldability of a sheet (1) of the composite metal sheet type having a layer (7) which is interposed between two metal facing sheets (3,5) and comprises a polymer (8) having a filler of conductive particles (9). This process comprises measuring by means of a signal of given frequency f applied to two electrodes (11,13) disposed in facing relation to each other, each electrode being in contact with a corresponding metal facing sheet (3,5), the voltage/current phaseshift $\phi$ due to the resistive and capacitive properties of the composite sheet (1). The response of the composite sheet (1) to this signal corresponds to that of an equivalent parallel RC circuit. Thereafter, the mass fraction of the conductive particles (9) is calculated from the value of $\phi$. By comparing the determined mass fraction with prefixed thresholds, the weldability and the vibration-damping capacity of the composite sheet (1) are evaluated.

12 Claims, 1 Drawing Sheet

PROCESS AND DEVICE FOR DETERMINING THE MASS FRACTION OF ONE CONSTITUENT OF A LAYER, AND EFFECTING THE QUALITY CONTROL OF A COMPOSITE METAL SHEET

The invention relates to the quality control of sheets of the composite metal sheet type and more particularly to the continuous control of the weldability of such sheets.

Composite metal sheets have vibration-damping properties which are used in particular for reducing the propagation of noise. They are used for example for manufacturing vehicle body elements in the motor industry or covering panels of domestic appliances of electrical household equipment.

Known composite metal sheets usually comprise two metal facing or cladding sheets separated by a film of synthetic material, such as for example a polymer which constitutes not only an acoustic but also an electric insulation.

For assembling composite metal sheets of large size it is current practice to interconnect the two sheets by resistance welding.

Now, as the polymer layer is insulating, the very widely used technique of resistance welding cannot be applied to conventional composite metal sheets.

To overcome this drawback, when manufacturing composite metal sheets, the layer of synthetic material is provided with a filler of a conductive material usually formed by balls of nickel so that the latter are in contact with the two metal facing sheets to ensure the electrical continuity of the sheet. To interconnect two sheets manufactured in this way, two of their end portions are superimposed and gripped between two electrodes through which a high electric current is passed. The passage of the electric current through the nickel balls distributed in the film of synthetic material results in a high heating that locally melts the metal facing sheets of the composite metal sheets which become welded under the effect of a pressure exerted by the electrodes.

It will therefore be understood that, in order to ensure the weldability by resistance of such composite metal sheets, the filler of conductive particles must be distributed in a sufficient amount in the synthetic material; an excessive amount of filler should however be avoided in order to conserve the acoustic insulating properties of the composite metal sheet. Generally, a filler of conductive particles of about a 20% mass fraction of the layer interposed between the metal facing sheets is used for ensuring the resistance weldability of composite metal sheets, at least a mass fraction of 5% being necessary.

To guarantee the resistance weldability of composite metal sheets, measuring means must be used for controlling the quantity of the filler of conductive particles in the layer interposed between the two metal facing sheets.

At the present time, two processes are known for evaluating the resistance weldability of composite metal sheets.

A first process comprises taking a sample of a composite metal sheet and effecting a few spot welds, namely about thirty spot welds, on this sample. The great drawback of this control or inspection process resides in the fact that it is destructive since the sample is rendered unusable by the control spot welds for a subsequent application. A thorough control of the manufacture of composite metal sheets requires a large number of samples which considerably increases the manufacturing costs.

Further, this process cannot be applied to the continuous control of a strip of composite metal sheet, for example a sheet leaving an installation manufacturing such sheets.

A second process is based on X-ray photographs which reveal the presence of conductive particles contained in the composite metal sheets. The main drawbacks of this process are the high cost of carrying out the process and the danger to the personnel owing to the powerful X-ray radiation in an industrial context. Moreover, this process rapidly reaches its limits of application when the thickness of the facing sheets of the composite metal sheet becomes excessive.

An object of the invention is to overcome these drawbacks by providing a process for controlling the weldability of a composite metal sheet which is non destructive, reliable, inexpensive and presents no danger to the personnel.

The invention therefore provides a process for determining the mass fraction of at least one of two constituents, one of which is formed by the conductive particles and the other is formed by an electrically insulating material, of a layer interposed between two metal facing sheets which together form with said interposed layer a composite metal sheet, said conductive constituents establishing an electric contact between the two metal facing sheets, characterized in that it comprises:

measuring, by means of a signal of given frequency f applied to two electrodes disposed in facing relation to each other, each electrode being in contact respectively with a corresponding metal facing sheet, the voltage/current phase shift,$\phi$, due to the resistive and capacitive properties of the composite metal sheet, likening the portion of the composite metal sheet between the electrodes to an equivalent parallel RC circuit, and calculating from the value of tan $\phi$ which is the expression of the ratio between the capacitive component and the resistive component of the impedance of the equivalent RC circuit, the mass fraction $Y_R, Y_C$ of at least one of said constituents, the mass fractions of these constituents being given by the following respective relations:

$$Y_R = \frac{1}{1 - \lambda \tan \phi} \text{ and}$$

$$Y_C = \frac{-\lambda \tan \phi}{1 - \lambda \tan \phi}$$

Where $\lambda$ is a constant determined by the frequency f of the signal applied to the two electrodes, by the electrical properties of each constituent of the layer interposed between the metal facing sheets and by the densities of said constituents.

The invention also provides a process for the quality control of a composite metal sheet comprising two metal facing sheets between which there is interposed a layer comprising two constituents, namely an electrically insulating material and conductive particles establishing an electric contact between the two metal facing sheets, characterized in that it comprises:

determining the mass fraction of one of the two constituents of the layer interposed between the two metal facing sheets and applying the process defined hereinbefore, fixing at least one threshold of the mass fraction of the constituent whose mass fraction has been determined, said threshold corresponding to a required property of the composite metal sheet, and comparing the value of the measured mass fraction with the fixed threshold for determining whether the composite metal sheet satisfies or does not satisfy the required property.

The invention further provides a device for effecting the quality control of a composite metal sheet which employs the process defined hereinbefore, characterized in that it comprises two electrodes disposed in facing relation to each other, each electrode being in contact respectively with a corresponding metal facing sheet of the composite metal sheet and being connected to the input of a unit for measuring the voltage/current phase shift, $\phi$, the output of the measuring unit being connected to the input of a utilization unit which calculates the mass fraction of said constituents of said layer and compares the mass fraction obtained with at least one predetermined threshold corresponding to a property of said composite metal sheet for determining whether the composite metal sheet satisfies or does not satisfy the required property.

Further features and advantages of the invention will appear from the following description which is given merely by way of a non-limitative example with reference to the accompanying drawings, in which.

Figure 1:
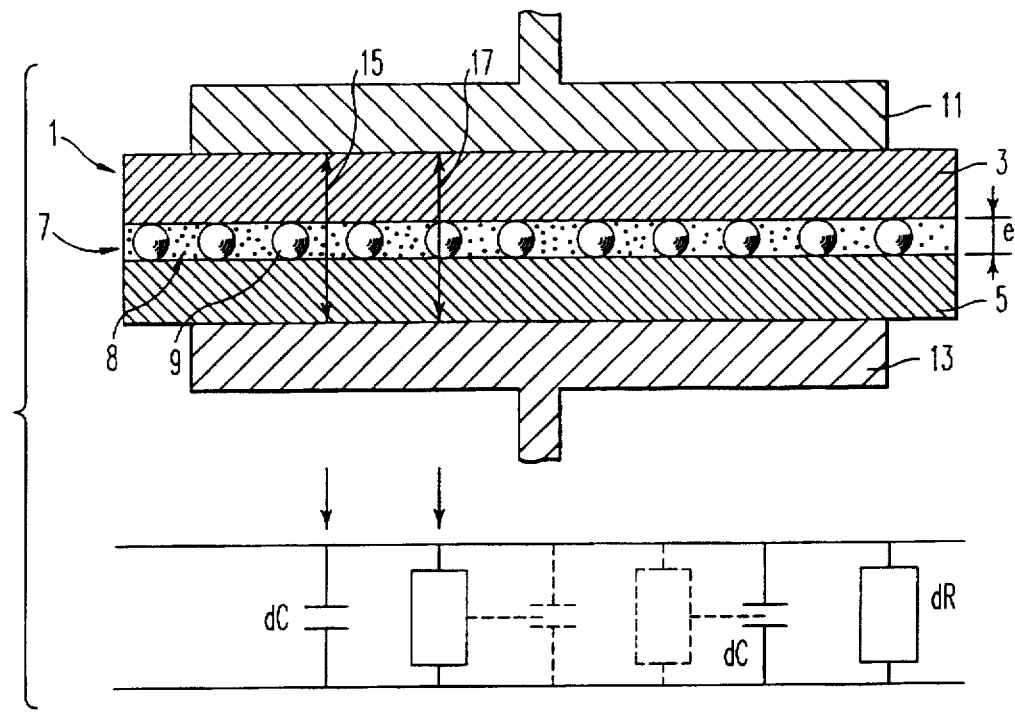
FIG. 1 is a sectional view of a composite metal sheet between two measuring electrodes and an equivalent electric circuit representing the electrical properties of the composite metal sheet.

FIG. 1 shows a composite metal or plymetal sheet 1 comprising two metal facing or cladding sheets 3 and 5. A layer 7 comprising an electrically and acoustically insulating material 8, for example a polymer, and a filler of conductive particles 9, for example balls of nickel, interposed between said facing sheets 3 and 5. The nickel balls 9 generally have a diameter of 50 μm and are uniformly distributed in the layer 7. The spacing e between the metal facing sheets 3 and 5 is such that the nickel balls 9 are in contact with both of the two metal facing sheets 3 and 5 to ensure an electrical continuity between the facing sheets.

An electrode 11, 13 is respectively applied to each metal facing sheet 3,5. These two electrodes are disposed in facing relation to each other and the composite metal sheet is interposed therebetween.

To characterize the electrical properties of such a composite metal sheet 1 in response to a signal of frequency f applied to the electrodes 11 and 13, the passage of a current from one facing sheet to the other is analysed along two current lines 15 and 17, one line 15 only passing through the polymer 8 of the layer 7, the other line 17 passing through a nickel ball 9.

Along the current line 15, the polymer 8 constitutes an electrical insulation between the two metal facing sheets 3 and 5. In this region, the composite metal sheet may be likened to an elementary capacitance dC.

Along the current line 17, the current passes through a nickel ball 9 which establishes an electric current between the two metal facing sheets 3 and 5, the current being limited by the electric resistance of the ball which depends on the particular resistivity $\sigma_R$ of the nickel. In this region, the composite metal sheet may be likened to an elementary resistance dR.

Consequently, the layer 7 formed by the polymer 8 including a filler of conductive particles 9 and interposed between the facing sheets 3 and 5 of the composite metal sheet may be likened to a succession of elementary resistances and capacitances, respectively dR and dC, arranged in parallel as shown in the lower part of FIG. 1.

The arrows at the ends of the current lines 15 and 17 indicate which one of the elementary electrical properties of the composite metal sheet is associated with each current line 15,17.

The elementary impedance of an association in parallel of dR and dC carrying an alternating current of frequency f is given by the following relation:

$$dZ = \frac{dR}{1 + jdRdC2\pi f} \tag{1}$$

The elementary resistance dR and the elementary capacitance dC are expressed as a function of the elementary areas $dA_R$ and $dA_C$ of passage of the current lines respectively in the resistive and capacitive parts of the sheet. The total area $A_R + A_C$ of passage of the current lines corresponds to the area of the confronting metal facing sheets through which the whole of the current passes. In a first approximation, it is considered that this total area $A_R + A_C$ corresponds to the area of contact between the metal facing sheets 3,5 and the electrodes 11,13.

The elementary resistance dR for the conductive particles 9 composed of a material of resistivity $\sigma_R$ is determined by:

$$dR = \frac{\sigma_R e}{dA_R} \tag{2}$$

In considering the dielectric permittivity $\epsilon$ of the polymer 8 between the facing sheets 3 and 5, there is obtained the elementary capacitance dC:

$$dC = \frac{\epsilon dA_C}{e} \tag{3}$$

By combining the equations (1), (2) and (3) there is obtained the total impedance $Z_T$ given by the arrangement in parallel of the elementary impedances dZ:

$$\frac{1}{Z_T} = \int_{A_R + A_C} \frac{1}{dZ} = \frac{A_R}{\sigma_R e} + j\frac{2\pi \epsilon f A_C}{e} \tag{4}$$

The resistive and capacitive properties of the layer 7 are therefore given by the connection in parallel of a resistance corresponding to a total resistive effect proportional to the amount of conductive particles and a resistance corresponding to a total capacitive effect proportional to the amount of polymer. The proportion of each of these effects is equal, apart from a constant factor, to the ratio of the sections of passage of current $A_R$ and $A_C$ through the conductive particles and through the polymer respectively. In considering the equation (4) and in calculating in the known manner tan $\phi$, where $\phi$ is the voltage/current phase shift caused by the total impedance $Z_T$, there is obtained, taking into account the fact that the thickness e of the layer 7 is constant, the ratio of the volumes $V_C$ and $V_R$ occupied respectively by the polymer 8 and the conductive particles 9 in this layer 7 by the following relation:

$$\frac{V_c}{V_R} = -\frac{\tan\phi}{\epsilon\sigma_R 2\pi f} \tag{5}$$

It is this ratio which permits deducing the mass fraction of one of the two constituents of the layer 7 interposed between the two metal facing sheets from the measure of a magnitude related to the resistive and capacitive properties of the composite metal sheet.

Knowing the densities $\rho_C$ and $\rho_R$ of the polymer and the conductive particles respectively, there is obtained the mass fraction of the conductive particles $Y_R$ distributed in the polymer from the relation:

$$Y_R = \frac{1}{1 + \frac{\rho_C}{\rho_R} \frac{V_C}{V_R}} \quad (6a)$$

The mass fraction of the polymer $Y_C$ is obtained from the relation:

$$Y_C = \frac{1}{1 + \frac{\rho_R}{\rho_C} \frac{V_R}{V_C}} \quad (6b)$$

In combining each equation (6a) and (6b) with the equation (5), there are then obtained the mass fractions $Y_R$ and $Y_C$ expressed with known parameters from the following relations:

$$Y_R = \frac{1}{1 - \lambda \tan\phi} \quad (7a)$$

$$Y_C = \frac{-\lambda \tan\phi}{1 - \lambda \tan\phi} \quad (7b)$$

where $\lambda$ is a constant for a given frequency f. $\lambda$ is given by the relation:

$$\lambda = \frac{\rho_C}{\rho_R} \frac{1}{\epsilon \sigma_R 2\pi f} \quad (8)$$

The mass fractions of the polymer and the conductive particles always satisfy the following relation:

$$Y_C + Y_R = 1 \quad (9)$$

Consequently, the determination of one of the two mass fractions $Y_C$ or $Y_R$ permits deducing the other by subtraction.

To determine the mass fraction of the conductive particles by applying the relation (7a), the phase shift $\phi$ may be measured by two known methods.

A first method comprises measuring the impedance $Z_R$ between the two electrodes 11 and 13 in contact respectively with one of the two metal facing sheets 3 and 5 by means of a signal of given frequency f. There are then extracted from the value of the impedance $Z_T$ the equivalent resistance R and the reactance X. Then tan $\phi$ is determined by calculating the ratio between the reactance X and the equivalent resistance R.

A second method comprises measuring by means of a signal of given frequency f the delay dT between an alternating voltage applied to the electrodes 11, 13 and the alternating current produced by this voltage. Knowing the frequency f and said delay dT, the phase shift $\phi$ and then tan $\phi$ are calculated.

Figure 2:
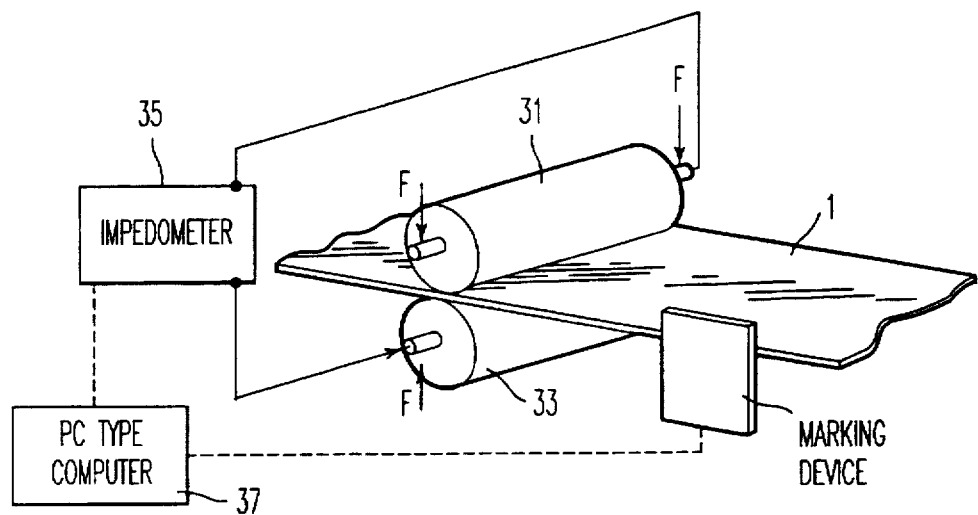
FIG. 2 is a diagrammatic perspective view of a device for the quality control of a travelling composite metal sheet strip.

An example of a device for determining the mass fraction and effecting the quality control of a composite metal sheet is shown in FIG. 2.

This arrangement comprises two electrodes 31 and 32 in the form of rollers between which a section of a travelling strip of composite metal sheet 1 is gripped, the widths of the rollers 31 and 33 and the strip being substantially equal. Of course it is not absolutely necessary that the width of the rollers 31 and 33 be equal to that of the strip. The two rollers 31 and 33 are rotatively mounted in a frame (not shown) so that the gripping force exerted on the composite metal sheet by the rollers 31,33 shown by the arrows F, may be adjusted, the axes of rotation of the rollers 31 and 33 being substantially perpendicular to the direction of travel of the strip. The strip of the composite metal sheet 1 travels between the rollers 31 and 33 and the determination of the mass fraction of one of the two constituents of the layer 7 according to the process of the invention is effected during this travel. The rollers 31 and 33 are made of a material having a low electric resistance, for example copper.

Each of the two electrodes formed by the two rollers 31 and 33 is electrically connected to an input of a measuring unit 35, for example an impedometer known per se. The impedometer 35 delivers an output signal corresponding to the module of the voltage/current phase shift $\phi$. As the composite metal sheet only has resistive and capacitive properties, the phase shift signal is determined. The output of the impedometer 35 is connected to the input of a utilization unit 37, for example a PC type computer. This PC 37 is programmed to calculate the mass fractions of the two constituents of the layer 7 by applying the relations (7a and (7b) or the relation (9) in combination with either of the relations (7a) and (7b) and to record them. The PC 37 is advantageously fed with a computer program which enables it to carry out the thresholding and comparison operations, described hereinafter, for determining whether the composite metal sheet 1 has or does not have one of the required properties such as weldability or vibration damping. Further, the PC 37 controls a device for marking the sheet (not shown) in the event that the latter does not meet the required conditions of quality.

To control the quality of a composite metal sheet as concerns its resistance weldability and its vibration damping properties, there is first of all determined, by means of the aforementioned device, the mass fraction for example of the conductive particles 9 uniformly distributed in the polymer 8 of the layer 7. Thereafter, the value obtained is compared with a predetermined minimum threshold $Y_R^{min}$, for example $Y_R^{min}=5\%$, and with a predetermined maximum threshold $Y_R^{MAX}$, for example $Y_R^{MAX}=20\%$. Below $Y_R^{min}$, the welding of the sheet is no longer possible and above $Y_R^{MAX}$, the vibration damping capacities are greatly diminished. If the given value of the mass fraction is not within the range defined by these minimum and maximum thresholds, it is considered that the composite metal sheet is of poor quality. In the opposite case, the composite metal sheet meets the required conditions of quality.

It will be understood that, for the purpose of quality control, it is also possible to determine the mass fraction $Y_C$ of the insulating material 8 by fixing the corresponding minimum threshold $Y_C^{min}$ and the maximum threshold $Y_C^{MAX}$. Below $Y_C^{min}$, the vibration damping capacities are greatly diminished and above $Y_C^{MAX}$ the welding of the sheet is no longer possible.

According to another embodiment of a device for determining the mass fraction and effecting the quality control of a composite metal sheet (not shown), the arrangement comprises two electrodes in the form of wheels which are moved transversely over the entire width of the travelling strip of composite metal sheet so as to achieve a scanning of the strip during its travel. These two rotary wheels then replace the two rollers and are mounted to be rotatable and movable in translation in a frame similar to that described in respect of the embodiment shown in FIG. 2.

What is claimed is:

1. Process for determining the mass fraction of at least one of two constituents of a layer, one of said constituents being formed by conductive particles and the other of said constituents being formed by an electrically insulating material, said layer being interposed between two metal facing sheets which together form with said interposed layer a composite metal sheet, said conductive constituent establishing an electric contact between said two metal facing sheets, characterized in that it comprises:

measuring a voltage/current phase shift $\phi$ due to the resistive and capacitive properties of the composite metal sheet by applying a signal of given frequency f to two electrodes disposed in facing relation to each other, each electrode being in contact with a respective one of said metal facing sheets;

modeling a portion of said composite metal sheet between said electrodes as an equivalent parallel RC circuit; and calculating, from the value of tan $\phi$ which is the expression of the ratio between the capacitive component and the resistive component of the impedance of said equivalent RC circuit, the mass fraction of at least one of said constituents, the mass fractions of said constituents being given by the following respective relations:

$$Y_R = \frac{1}{1 - \lambda \tan \phi} \text{ and}$$

$$Y_C = \frac{-\lambda \tan \phi}{1 - \lambda \tan \phi}$$

where $\lambda$ is a constant determined by said frequency f of said signal applied to said two electrodes, by the electrical properties of each constituent of said layer interposed between said metal facing sheets and by the densities of said constituents, and where $Y_R$ is the mass fraction of the resistive component and $Y_C$ is the mass fraction of the capacitive component.

2. Process according to claim 1, comprising calculating said mass fraction of the other constituent whose mass fraction was not determined, by the relation:

$$Y_C + Y_R = 1.$$

3. Process for effecting the quality control of a composite metal sheet comprising two metal facing sheets between which is interposed a layer comprising two constituents, one of said constituents being formed by conductive particles establishing an electric contact between said two metal facing sheets, and the other of said constituents being formed by an electrically insulating material, said process comprising:

determining the mass fraction of one of said two constituents of said layer by:

measuring a voltage/current phase shift $\phi$ due to the resistive and capacitive properties of the composite metal sheet by applying a signal of given frequency f to two electrodes disposed in facing relation to each other, each electrode being in contact with a respective one of said metal facing sheets;

modeling a portion of said composite metal sheet between said electrodes to an equivalent parallel RC circuit; and calculating from the value of tan $\phi$, which is the expression of the ratio between the capacitive component and the resistive component of the impedance of said equivalent RC circuit, the mass fraction of at least one of said constituents, the mass fractions of said constituents being given by the following respective relations:

$$Y_R = \frac{1}{1 - \lambda \tan \phi} \text{ and}$$

$$Y_C = \frac{-\lambda \tan \phi}{1 - \lambda \tan \phi}$$

where $\lambda$ is a constant determined by said frequency f of said signal applied to said two electrodes, by the electrical properties of each constituent of said layer interposed between said metal facing sheets and by the densities of said constituents, and where $Y_R$ is the mass fraction of the resistive component and $Y_C$ is the mass fraction of the capacitive component, said process further comprising:

fixing at least one threshold of the mass fraction of the constituent whose mass fraction has been determined, said threshold corresponding to a required property of said composite metal sheet, and comparing the value of the determined mass fraction with the fixed threshold for determining whether said composite metal sheet satisfies or does not satisfy said required property.

4. Process according to claim 3, wherein said required property of said composite metal sheet is the resistance weldability of such a composite sheet and said fixed threshold of said mass fraction constitutes a minimum threshold when the mass fraction of said conductive particles is being determined and a maximum threshold when the mass fraction of said insulating material is being determined.

5. Process according to claim 3, wherein said required property of said composite metal sheet is its vibration-damping capacity and said fixed threshold of said mass fraction constitutes a maximum threshold when the mass fraction of said conductive particles is being determined and a minimum threshold when the mass fraction of said insulating material is being determined.

6. Process according to claim 3, comprising fixing two thresholds of said mass fraction, one corresponding to the weldability of said composite metal sheet and the other corresponding to a vibration-damping capacity of said composite metal sheet.

7. Process according to claim 3, wherein said composite metal sheet is a travelling strip of a composite metal sheet and at least one mass fraction of one of said two constituents of said layer is measured in the course of said travel.

8. Device for effecting the quality control of a composite metal sheet comprising two metal facing sheets between which is interposed a layer comprising two constituents, one of said constituents being formed by conductive particles establishing an electric contact between said two metal facing sheets, and the other of said constituents being formed by an electrically insulating material, comprising:

by means of a process comprising:

determining the mass fraction of one of said two constituents of said layer by:

measuring by means of measuring a voltage/current phase shift $\phi$ due to the resistive and capacitive properties of the composite metal sheet by applying a signal of given frequency f applied to two electrodes disposed in facing relation to each other, each electrode being in contact with a respective one of said metal facing sheets;

modeling a portion of said composite metal sheet between said electrodes as an equivalent parallel RC circuit;

calculating, from the value of tan $\phi$, which is the expression of the ratio between the capacitive component and the resistive component of the impedance of said equivalent RC circuit, the mass fraction of at least one of said constituents, the mass fractions of said constituents being given by the following respective relations:

$$Y_R = \frac{1}{1 - \lambda \tan \phi} \text{ and}$$

$$Y_C = \frac{-\lambda \tan \phi}{1 - \lambda \tan \phi}$$

where $\lambda$ is a constant determined by said frequency f of said signal applied to said two electrodes, by the electrical properties of each constituent of said layer interposed between said metal facing sheets and by the densities of said constituents, and where $Y_R$ is the mass fraction of the resistive component and $Y_C$ is the mass fraction of the capacitive component;

fixing at least one threshold of the mass fraction of the constituent whose mass fraction has been determined, said threshold corresponding to a required property of said composite metal sheet; and comparing the value of the measured mass fraction with the fixed threshold for determining whether said composite metal sheet satisfies or does not satisfy said required property;

said device comprising in combination:

two electrodes disposed in facing relation to each other, each electrode being in contact with a respective one of said metal facing sheets, a unit for measuring the voltage/current phase shift $\phi$ having an inlet and an outlet, each electrode being connected to said input of said unit for measuring, a utilization unit having an input connected to said outlet of said unit for measuring, for calculating the mass fraction of said constituents of said layer and comparing the mass fraction obtained with at least one predetermined threshold corresponding to a property of said composite metal sheet for determining whether said composite metal sheet satisfies or does not satisfy the required property.

9. Device according to claim 8, wherein said electrodes are in the form of rollers in contact with a travelling strip of said composite metal sheet and are rotatively mounted in a frame, said rollers exerting an adjustable gripping force on said strip.

10. Device according to claim 8, wherein said utilization unit is a computer loaded with a computer program which effects steps of calculating and effecting a comparison with predetermined thresholds, said device further comprising a device for marking said sheet in the event that said sheet does not have said required quality, said computer being operatively connected to said marking device.

11. Device according to claim 9, wherein said utilization unit is a computer loaded with a computer program which effects the steps of calculating and effecting a comparison with predetermined thresholds, said device further comprising a device for marking said sheet in the event that said sheet does not have said required quality, said computer being operatively connected to said marking device.

12. Device according to claim 8, wherein said measuring device is an impedometer.

* * * * *